United States Patent [19]

Finch et al.

[11] 4,211,718
[45] Jul. 8, 1980

[54] METHANATION PROCESS

[75] Inventors: Jack N. Finch; Forrest L. Poska, both of Bartlesville, Okla.

[73] Assignee: Phillips Petroleum Company, Bartlesville, Okla.

[21] Appl. No.: 927,080

[22] Filed: Jul. 24, 1978

[51] Int. Cl.$^2$ ................................................ C07C 1/04
[52] U.S. Cl. ............................. 260/449 M; 252/411 S
[58] Field of Search .................. 260/449 M, 449.6 M; 252/411 S

[56] References Cited

U.S. PATENT DOCUMENTS

| | | | |
|---|---|---|---|
| 2,455,419 | 12/1948 | Johnson | 252/411 S |
| 3,615,164 | 10/1971 | Baker et al. | 260/449 M |
| 4,079,072 | 3/1978 | Finch | 260/449 M |

*Primary Examiner*—Howard T. Mars

[57] ABSTRACT

Methane is prepared by contacting carbon monoxide and hydrogen in the presence of a supported iridium-containing or rhodium-containing catalyst and a small, effective amount of steam to maintain methanation catalyst activity. In another embodiment, the methanation activity of supported iridium-containing and rhodium-containing catalysts lost due to sulfur poisoning is restored by contacting the catalyst with a sulfur-free feed of carbon monoxide and hydrogen under methanation conditions in the presence of a small, effective amount of steam for a period of time sufficient to substantially restore methanation catalyst activity.

9 Claims, No Drawings

METHANATION PROCESS

This invention relates to the production of methane. In accordance with another aspect, this invention relates to an improved catalyst system for the production of methane. In yet another of its aspects, this invention relates to a process for restoring methanation catalyst activity of sulfur-poisoned catalysts. In accordance with another aspect, supported iridium-containing and rhodium-containing methanation catalysts that have been sulfur-poisoned are contacted with a sulfur-free methanation feed and a small amount of steam under methanation conditions to restore methanation catalyst activity.

The manufacture of methane as a substitute natural gas will become increasingly important in the furture as deposits of natural gas become depleted while the demand continues. An important route to manufacturing methane is the hydrogenation of carbon monoxide. Although this reaction has been known since 1902, it still suffers from some technological problems. Important among these problems is the fact that commonly available sources of carbon monoxide, e.g., coal and lignite, via the carbon-steam reaction, invariably contain enough sulfur which, if not removed, would poison completely the common methanation catalysts such as nickel. When this happens, the catalyst must be discarded and replaced since there is no presently known way to rejuvenate it. While it will continue to be necessary to remove essentially all of the sulfur from methane—natural or substitute—to protect the consumer, it would be helpful if the catalyst on which carbon monoxide is methanated could tolerate continuous traces or occasional overdoses of sulfur without requiring catalyst replacement.

The present invention is directed to improved methanation catalysts and to the restoration of catalyst activity of sulfur-poisoned methanation catalysts.

Accordingly, an object of this invention is to provide an improved process for methanation.

A further object of this invention is to provide an improved process for producing methane from carbon monoxide and hydrogen.

A further object of this invention is to provide a process for restoring catalyst activity of sulfur-poisoned methanation catalysts.

Other objects, aspects, and the several advantages of this invention will be apparent to those skilled in the art upon a study of this specification and the appended claims.

In accordance with the present invention, a process is provided for producing methane which comprises contacting hydrogen with carbon monoxide and a small amount of steam in the presence of a catalyst comprising at least one of iridium and rhodium and a support.

In accordance with another embodiment of the invention, sulfur-poisoned methanation catalysts comprising supported iridium-containing and rhodium-containing catalysts are restored for methanation activity by contacting with a sulfur-free feed of carbon monoxide and hydrogen with a small amount of steam under methanation conditions for a period of time sufficient to substantially restore the activity of the sulfur-poisoned catalyst.

It has been found that if the sulfur-free synthesis gas contains from about one to about 30 mole percent of steam, the sulfur-poisoned iridium and rhodium catalysts regain essentially all of the initial methanation activity at similar conditions. Thus, the present invention provides a catalyst and a process that can accommodate periodic sulfur poisoning without suffering permanent damage.

In accordance with a further embodiment of the invention, supported rhodium-containing and iridium-containing catalysts exhibit good recovery from sulfur poisoning when the poisoned catalysts are contacted in situ under methanation conditions with a sulfur-free methanation feed containing from about one to about 30 mole percent steam.

Methanation of synthesis gas comprising hydrogen and carbon monoxide, generally at a stoichiometric molar ratio of about 3:1, over supported iridium-containing and rhodium-containing catalysts, is effected in this invention. It has been found that such catalysts when poisoned by a sulfur compound such as $CS_2$, $H_2S$, etc., can be restored in activity by contacting the catalysts under methanation conditions with synthesis gas and a small amount of steam. By poisoning is meant that a sufficient amount of a sulfur compound has contacted that catalyst to suppress its methanation activity to a low level. The amount of sulfur compound added generally exceeds that required to cover the catalytic sites on the surface of the catalyst and in most cases is sufficient to form the metal sulfide or sulfides. Methane produced can be recovered from the effluent and used as synthetic natural gas or for other purposes, if desired. The synthesis gas feed can be made by conventional steam reforming of hydrocarbons, i.e., naphtha, and coal char, by blending hydrogen and carbon monoxide obtained from suitable refinery or chemical process streams, and the like.

The catalysts of this invention comprise iridium and/or rhodium supported on a refractory, particulate substrate selected from alumina, silica-alumina, silica, Group II titanates such as calcium titanate, zinc titanate, and the like.

The concentration of iridium and rhodium in the catalyst, calculated as the element, can vary appreciably but the amount of total metal present will be sufficient to provide a catalyst effective for the methanation reaction. In general, the total amount of rhodium and iridium present can range between about 0.05 to 5 percent of the weight of the support. Preferably, the concentration will be between about 0.1 to 2 weight percent, and still more preferably from about 0.5 to 1 weight percent. To utilize the metals most efficiently, the preferred method of adding the metals to the support is by impregnation with a rhodium and iridium compound solution, although dry mixing is not precluded. Suitable rhodium and iridium salts include the hydrated chloride and other simple halides, nitrate, sulfate, sulfite, and complexes, both cationic and anionic, such as $[Rh(NH_3)_6]X_3$ and $M_3^1[RhX_6]$ where $M^1$ is a univalent metal and X can be Cl, $NO_2$, CN, $\frac{1}{2}SO_4$, $\frac{1}{2}SO_3$, $\frac{1}{2}C_2O_4$, etc. Solvents for the rhodium and iridium compounds can be water or non-aqueous liquids such as alcohols, ethers, hydrocarbons, and the like—chosen for their ability to dissolve the compound. After impregnation, the catalyst is dried in an oxygen-containing atmosphere such as air at a temperature that removes solvent expeditiously, then heated in air or other oxygen-containing gas at about 400° to 600° C. to remove volatile or organic material. Finally, to enhance the initial activity of the catalyst, it is preferred to heat it in a stream of hydrogen at about 300°–600° C. before initiating the methanation process.

The feed gas to a methanation reactor ideally contains only hydrogen and carbon monoxide, in the respective mole ratio of 3:1, with no catalyst poisons. In practice, it will generally also contain impurities such as nitrogen and carbon dioxide and occasionally, perhaps because of maloperation, some sulfur compounds. The mole ratio of hydrogen to carbon monoxide can range from about 1:1 to 4:1; preferably the ratio will be nearer to the stoichiometric, between about 2:1 to 3:1. Ratios greater than about 3:1 are wasteful of hydrogen and are preferably avoided.

The methanation conditions that can be used include temperatures, pressures, and contact times sufficient to produce methane from the synthesis gas. The methanation conditions employed apply to normal operation as well as conditions employed for restoration of catalyst activity when it is desired to increase methanation activity and decrease water gas shift activity of the catalyst. In general, reaction temperature for catalytic methanation can range from about 200° to about 600° C., preferably between about 300° to 575° C., and most preferably it will be about 550° C.

In general, reaction pressure for methanation can range from about atmospheric to 12,000 psig (82.7 megapascals). Since a decrease in volume accompanies the reaction, it will be favored by higher pressure.

In general, gaseous hourly space velocity (GHSV) of synthesis gas—volumes of gas at STP per volume of catalyst per hour—can range between about 200 and 10,000. Good results have been obtained at about 600 to 5,000.

If the synthesis gas being fed to methanation is completely and assuredly free from sulfur compounds that could poison the instant catalysts, operation with no steam being added to the feed is the preferred mode. Except in very unusual circumstances this condition never obtains. Then, it is desirable to include some steam in the synthesis gas. The reason for its efficacy is not clearly understood at present, but is believed that steam either aids in the desorption of sulfur residing on active sites or hastens decomposition of the inactive sulfides on the catalyst. Generally the concentration of steam in the feed will be in the range of about one to 30 mole percent. A preferred range is about 5 to 10 mole percent. Use of excessive concentration of steam will cause a wasteful loss of carbon monoxide via the water gas shift reaction.

Since methanation catalysts are active to catalyze the water gas shift reaction, carbon monoxide is converted to both methane and carbon dioxide. Consequently the expression of experimental results must be clearly defined. Here an expression proposed by the Institute of Gas Technology ["Pipeline Gas from Coal by Methanation of Synthesis Gas," Institute of Gas Technology Research Bulletin No. 31 (1963)] is used which defines conversion of hydrogen and carbon monoxide on an equal basis:

$$\text{Conversion (\%)} = 100 \cdot 4 \cdot \frac{\text{moles dry product gas}}{\text{moles dry synthesis gas}} \times \text{mole fraction } CH_4 \text{ in dry product gas}$$

In actual operation, the supported iridium-containing and rhodium-containing catalysts, in effective amounts, are contacted with a feed stream comprising carbon monoxide and hydrogen under methanation reaction conditions such that said catalysts are poisoned due to the presence of sulfur in the feedstream, then the catalysts lose methanation activity; and, in accordance with one embodiment of the invention, the methanation catalyst activity can be restored by contacting the sulfur-poisoned catalyst with a sulfur-free methanation feed comprising carbon monoxide and hydrogen and steam under methanation conditions, preferably about 550° C., and the contacting is continued until the activity of the sulfur-poisoned catalyst is substantially restored so that methanation can be continued by contacting of the catalyst having restored activity with new methanation feed. The length of time that the sulfur-poisoned catalyst is contacted with the sulfur-free feed and steam under methanation conditions is continued for a period of time sufficient to substantially restore the activity of the catalyst, and this will ordinarily range from about one to about 100 hours.

The practice of this invention is illustrated by the following examples.

EXAMPLE I

Catalyst Preparation. A solution containing $7.2 \times 10^{-3}$ gm rhodium per cc was prepared by dissolving rhodium (III) nitrate in water; 17.5 cc of this solution were added to 25.1 gm of $-16+60$ U.S. series sieve Harshaw Al 1404 alumina that had previously been heated two hours in air at 500° C. After standing about two hours at room temperature, the preparation was dried at 125° C. in an oven, then heated to 500° C. in flowing hydrogen gas prior to testing.

EXAMPLE II

Runs with 2.5:1 $H_2$:CO synthesis gas. The catalyst prepared as described in Example I was tested for its activity to methanate synthesis gas having 2.5 volumes hydrogen per volume carbon monoxide. All runs were made in three parts, as follows: (1) for 24 hours it was exposed to premixed synthesis gas under reaction conditions (described below) to measure its activity; (2) for the next 24 hours it was exposed to synthesis gas prepared by combining hydrogen containing 500 ppm $H_2S$ with carbon monoxide, at the same nominal flow rate; and (3) finally, testing with sulfur-free feed that was used initially was continued for 48 hours to observe the methanation activity. During the second interval, when sulfur-containing feed was used, the catalyst was exposed to about 13 moles of sulfur per mole of contained rhodium. All runs were made at 550° C., 115 psig (894 kilopascals), and about 1000–1300 GHSV; the concentration of steam being added to the synthesis gas during the 96 hours that each run required was the variable parameter being evaluated.

Table I summarizes the results of runs made at five different concentrations of steam in the feed. These ranged from zero to about 22 mole percent. Conversion values are based on analyses of samples taken at the end of the stated interval.

TABLE I

| Run No. | Run Condition | Steam Concentration, mole % | Feed Rate, GHSV | Conversion %, (IGT) | Selectivity to $CH_4$, % |
|---|---|---|---|---|---|
| 1 | Pre-sulfide | 0 | 1123 | 77.0 | 72.3 |
| 2 | Sulfided | 0 | 1351 | 28.5 | 62.4 |
| 3 | Recovered | 0 | 1255 | 69.7 | 67.9 |
| 4 | Pre-sulfide | 5.3 | 1049 | 81.9 | 74.4 |
| 5 | Sulfided | 4.7 | 1194 | 29.8 | 62.3 |

TABLE I-continued

| Run No. | Run Condition | Steam Concentration, mole % | Feed Rate, GHSV | Conversion %, (IGT) | Selectivity to $CH_4$, % |
|---|---|---|---|---|---|
| 6 | Recovered | 5.1 | 1080 | 78.2 | 71.4 |
| 7 | Pre-sulfide | 9.8 | 1102 | 75.6 | 68.9 |
| 8 | Sulfided | 8.5 | 1296 | 17.5 | 47.9 |
| 9 | Recovered | 10.2 | 1063 | 77.3 | 69.2 |
| 10 | Pre-sulfide | 18.0 | 1133 | 66.8 | 60.8 |
| 11 | Sulfided | 16.0 | 1299 | 10.0 | 22.7 |
| 12 | Recovered | 18.3 | 1106 | 72.8 | 64.3 |
| 13 | Pre-sulfide | 21.9 | 1185 | 67.5 | 60.7 |
| 14 | Sulfided | 20.6 | 1282 | 8.7 | 17.6 |
| 15 | Recovered | 22.4 | 1155 | 68.0 | 62.0 |

In every case, as expected, operation with sulfur-containing feed markedly depressed methanation as measured by CO conversion; and upon removal of sulfur from the feed, methanation activity increased. Note, however, that in the absence of added steam (Runs 1-3), recovered conversion was about 89 percent as large as the initial conversion was while in Runs 4-6 with about 5 mole percent steam, the recovered conversion was 95 percent of the initial and in Runs 7-9 with about 10 mole percent added steam, recovered conversion was 102 percent of the initial. At all higher steam concentrations, the recovered activity exceeded or equalled the initial activity. This is quite remarkable for a sulfided metal hydrogenation catalyst.

EXAMPLE III

Runs with 3:1 $H_2$:CO synthesis gas. The catalyst prepared as described in Example I was also evaluated for its activity to methanate synthesis gas having three volumes hydrogen per volume carbon monoxide. The run schedule and reaction conditions were identical to those given in Example II.

Table II summarizes runs made at six different concentrations of steam in the feed. These ranged from zero to about 22 mole percent. As in Example I, operation with the sulfur-containing synthesis gas substantially lowered methanation. However, it can be seen from the data that continuing operation with sulfur-free feed, particularly with added steam, restored catalyst activity. Note that in Runs 1-3, made without added steam, the catalyst recovered about 72 percent of its initial activity after being sulfided, but in Runs 4-6, with about 5 mole percent steam in the feed, 95 percent of the initial activity was regained. In Runs 7-9, with steam concentration increased to about 10 mole percent, the catalyst recovered 91 percent of its initial activity.

TABLE II

| No. | Test Condition | Steam Concentration, mole % | Feed Rate, GHSV | Conversion %, (IGT) | Selectivity to $CH_4$, % |
|---|---|---|---|---|---|
| 1 | Pre-sulfide | 0 | 1094 | 85.8 | 85.3 |
| 2 | Sulfided | 0 | 1092 | 32.3 | 62.9 |
| 3 | Recovered | 0 | 1125 | 62.1 | 72.6 |
| 4 | Pre-sulfide | 5.7 | 1000 | 87.7 | 84.6 |
| 5 | Sulfided | 5.1 | 1115 | 31.0 | 57.2 |
| 6 | Recovered | 5.5 | 1029 | 83.3 | 81.8 |
| 7 | Pre-sulfide | 9.7 | 1090 | 82.0 | 80.4 |
| 8 | Sulfided | 9.3 | 1142 | 27.1 | 49.0 |
| 9 | Recovered | 10.0 | 1047 | 74.6 | 78.2 |
| 10 | Pre-sulfide | 14.5 | 1003 | 83.3 | 80.6 |
| 11 | Sulfided | 13.2 | 1123 | 14.4 | 33.5 |
| 12 | Recovered | 14.0 | 1046 | 69.8 | 74.4 |
| 13 | Pre-sulfide | 18.6 | 1069 | 78.7 | 79.4 |
| 14 | Sulfided | 17.2 | 1176 | 12.5 | 26.6 |

TABLE II-continued

| Test No. | Condition | Steam Concentration, mole % | Feed Rate, GHSV | Conversion %, (IGT) | Selectivity to $CH_4$, % |
|---|---|---|---|---|---|
| 15 | Recovered | 18.8 | 1059 | 71.1 | 71.0 |
| 16 | Pre-sulfide | 22.5 | 1100 | 78.5 | 76.3 |
| 17 | Sulfided | 20.9 | 1209 | 8.9 | 17.7 |
| 18 | Recovered | 22.4 | 1109 | 61.8 | 65.0 |

Continuing to still higher steam concentrations resulted in lower extent of recovery, but in all cases the fraction of initial activity restored to sulfur-poisoned catalyst was significantly higher when steam was added to the synthesis gas than in its absence.

Although the runs to measure catalyst activity are based on analyses made after 48 hours of operation, product analyses made during that interval showed that in about ten hours the process of recovery had ended, i.e., essentially no further improvement was experienced after that.

EXAMPLE IV

Catalyst preparation. 10.00 g of 16-60 mesh (U.S. Series) Harshaw Al 1404 alumina were poured into 6.3 cc of chloroiridic acid solution containing $8.0 \times 10^{-3}$ g iridium per cc and the mixture was stirred and allowed to stand for two hours. The preparation was dried at 125° C. in an oven, then reduced in a stream of flowing hydrogen at 500° C. for two hours.

EXAMPLE V

A series of synthesis runs were made using a 3:1 $H_2$:CO molar ratio synthesis gas feed to test catalyst prepared as described in Example IV for methanation activity. All runs were made at 550° C., 115 psig (894 kilopascals) and about 1100-1250 GHSV. Steam was added to the feed gas as noted in the table for each run. Each run was carried out in three parts: (1) fresh catalyst was tested for 24 hours under synthesis reaction conditions; (2) for the next 24 hours the catalyst was poisoned by intermittent pulse injection of $H_2S$ into the synthesis gas feed, the total $H_2S$ injected being equivalent to about 15 atoms of sulfur per atom of iridium on the catalyst; and (3) sulfur-free feed was continued for 48 hours to observe the recovery of methanation activity. Table III summarizes the results of runs with iridium-impregnated alumina, both without steam and with three concentration levels of steam in the feed gas.

TABLE III

| Run | Run Conditions | Steam Concentration, Mole % | Feed Rate, GHSV | Conversion % (IGT) | Selectivity to $CH_4$, % |
|---|---|---|---|---|---|
| 19 | Pre-sulfide | 0 | 1085 | 58.4 | 70.2 |
| 20 | Sulfided | 0 | 1085 | 31.5 | 62.5 |
| 21 | Recovered | 0 | 1085 | 59.4 | 71.2 |
| 22 | Pre-sulfide | 4.8 | 1260 | 65.4 | 71.9 |
| 23 | Sulfided | 4.8 | 1260 | 41.8 | 61.7 |
| 24 | Recovered | 4.8 | 1260 | 74.2 | 77.7 |
| 25 | Pre-sulfide | 9.1 | 1244 | 52.2 | 65.0 |
| 26 | Sulfided | 9.1 | 1244 | 36.5 | 53.8 |
| 27 | Recovered | 9.1 | 1132 | 59.7 | 68.2 |
| 28 | Pre-sulfide* | 14.5 | 1068 | 53.0 | 61.2 |
| 29 | Sulfided | 14.5 | 1068 | 16.4 | 38.7 |
| 30 | Recovered | 14.5 | 1068 | 52.5 | 58.3 |

*For 23-hour period

As was the case with rhodium catalysts, in every run methanation activity was markedly depressed by exposure to sulfur-containing feed. In most cases, however, recovered conversion and selectivity was even higher than the initial values with fresh catalyst. Recovery was generally complete within about eight hours after the removal of sulfur from the feed.

We claim:

1. A process comprising contacting a sulfur-containing feedstream comprising carbon monoxide and hydrogen with a catalytically effective amount of a supported catalyst consisting of at least one of iridium and rhodium under methanation conditions and in the presence of a finite, effective, small amount of steam sufficient to increase methanation activity when said activity is affected by sulfur poisoning so that a predominant amount of carbon monoxide and hydrogen in the feedstream is converted to methane.

2. A process according to claim 1 wherein the amount of steam present ranges from about one to about 30 mole percent of the synthesis feed.

3. A process according to claim 2 wherein the amount of steam present ranges from about five to about ten mole percent.

4. A process according to claim 1 wherein said feedstream is contacted with said catalyst at a temperature in the range of from about 200° C. to about 600° C., a pressure in the range of about zero to about 12,000 psig, a GHSV of about 200 to about 10,000, and a molar ratio of hydrogen to carbon monoxide of about three.

5. A process according to claim 1 wherein the amount of rhodium and/or iridium present in the catalyst ranges from about 0.05 to about five percent by weight of a refractory support selected from alumina, silica-alumina, silica, and Group II titanates.

6. In a process comprising contacting a sulfur-containing feedstream of carbon monoxide and hydrogen with a supported catalyst consisting of at least one of iridium and rhodium under methanation conditions such that said carbon monoxide and hydrogen in said feedstream are converted to methane, and in which there is a loss of methanation activity caused by entry of sulfur into the feed and poisoning of said catalyst, the improvement for restoring methanation activity in situ of the sulfur-poisoned catalyst which comprises contacting said sulfur-poisoned catalyst under methanation conditions with a sulfur-free feed of carbon monoxide and hydrogen in the presence of steam in an amount ranging from about 1 to about 30 mole percent of the synthesis feed for a period of time sufficient to substantially restore the activity of said catalyst and continuing methanation by contacting said catalyst having restored methanation catalytic activity with carbon monoxide and hydrogen under methanation conditions such that a predominant amount of said carbon monoxide and hydrogen is converted to methane.

7. A process according to claim 6 wherein the amount of steam present ranges from about 5 to about 10 mole percent.

8. A process according to claim 6 wherein said methanation reaction conditions include a temperature of about 200° C. to about 600° C., a pressure in the range of about 0 to about 12,000 psig, a GHSV of about 200 to about 10,000 and a molar ratio of hydrogen to carbon monoxide from about 1:1 to 4:1.

9. A process according to claim 6 wherein said catalyst is a rhodium-alumina catalyst or an iridum-alumina catalyst.

* * * * *